United States Patent [19]

Roorda et al.

[11] Patent Number: 5,540,912
[45] Date of Patent: Jul. 30, 1996

[54] VISCOUS SUSPENSIONS OF CONTROLLED-RELEASE DRUG PARTICLES

[75] Inventors: Wouter E. Roorda, Newark; Fred Ehnow, Mountain View, both of Calif.

[73] Assignee: Alza Corporation, Palo Alto, Calif.

[21] Appl. No.: 307,843

[22] PCT Filed: Mar. 30, 1993

[86] PCT No.: PCT/US93/02992

§ 371 Date: Sep. 30, 1994

§ 102(e) Date: Sep. 30, 1994

[87] PCT Pub. No.: WO93/19739

PCT Pub. Date: Oct. 14, 1993

[51] Int. Cl.$^6$ ................................................. A61K 9/70
[52] U.S. Cl. ..................... 424/422; 424/426; 424/425; 424/484; 424/486; 514/818
[58] Field of Search .................................. 424/401, 426, 424/425, 484, 486, 435, 488, 422; 514/818, 947

[56] References Cited

U.S. PATENT DOCUMENTS

| | | | |
|---|---|---|---|
| 4,070,347 | 1/1978 | Schmitt | 260/77.5 |
| 4,093,709 | 6/1978 | Choi et al. | 424/19 |
| 4,122,158 | 10/1978 | Schmitt | 424/27 |
| 4,131,648 | 12/1978 | Choi et al. | 424/22 |
| 4,138,344 | 2/1979 | Choi et al. | 252/1 |
| 4,155,992 | 5/1979 | Schmitt | 424/19 |
| 4,180,646 | 12/1979 | Choi et al. | 528/153 |
| 4,249,531 | 2/1981 | Heller et al. | 128/260 |
| 4,351,337 | 9/1982 | Sidman | 128/260 |
| 4,780,320 | 10/1988 | Baker | 424/493 |
| 4,917,892 | 4/1990 | Speaker et al. | 424/401 |
| 4,919,939 | 4/1990 | Baker | 424/493 |
| 4,940,588 | 7/1990 | Sparks et al. | 424/486 |
| 4,962,091 | 10/1990 | Eppstein et al. | 514/2 |
| 4,994,281 | 2/1991 | Muranishi et al. | 424/497 |
| 5,008,117 | 4/1991 | Calanchi et al. | 424/494 |
| 5,183,662 | 2/1993 | Morita et al. | 424/426 |
| 5,332,576 | 7/1994 | Mantelle | 424/443 |

FOREIGN PATENT DOCUMENTS

| | | | |
|---|---|---|---|
| 0244118 | 11/1987 | European Pat. Off. | A61K 9/10 |
| WO9000048 | 1/1990 | WIPO | A61K 9/22 |
| WO9219226 | 11/1992 | WIPO . | |

OTHER PUBLICATIONS

Maninder Singh Hora, Rajsharan K. Rana, Jack H. Nunberg, Thomas R. Tice, Richard M. Gilley and Michael E. Hudson, "Controlled Release of Interleukin-2 from Biodegradable Microspheres", Bio/Technology, vol. 8, pp. 755–758, Aug., 1990.

Toshiro Heya, Hiroaki Okada, Yusuke Tanigawara, Yasuaki Ogawa and Hajime Toguchi, "Effects of Counte–anion of TRH and Loading Amount on Control of TRH Release from Copoly(dl–lactic acid) Microspheres Prepared by an In–Water Drying Method", International Journal of Pharmaceutics, vol. 69 (1991) pp. 69–75.

Wakiyama, Naoki; Juni, Kazuhiko and Nakano, Masahiro, "Preparation and Evaluation in Vitro of Polylactic Acid Microspheres Containing Local Anesthetics", Chem. Pharm. Bull., vol. 29, No. 11, pp. 3363–3368, (1981).

Juni, K., "Poly(Hydroxy Acids) in Drug Delivery", CRC Critical Reviews in Therapeutic Drug Carrier Systems, vol. 3, Issue 3, pp. 209–232.

Sinclair, R., Cassuto, J., Hogstrom, S., Linden, I., Faxen, A., Hedner, T. and Ekman, R., "Topical Anesthesia with Lidocaine Aerosol in the Control of Postoperative Pain", Anesthesiology, vol. 68, No. 6, Jun., 1988.

William D., et al. "Wound Dressing in Maxilli–facial Trauma" Abcor Report No. 2679–F (1979) Skin & Allergy News, vol. 21, No. 10, Says Antibiotic Microspheres Might Allow Better Wound Care.

Nakano, M. et al. "Biodegradable Microspheres for Prolonged Local Anesthesia", Ninth Cascade, p. 51.

Tice, T. R. and Cowsar, D. R., "Biodegradable Controlled–Release Parenteral Systems", Pharmaceutical Technology, Nov., 1984, pp. 26–34.

Primary Examiner—Thurman K. Page
Assistant Examiner—Sharon Howard
Attorney, Agent, or Firm—Richard T. Ito; Steven F. Stone; Mary Ann Dillahunty

[57] ABSTRACT

Controlled-release particles containing biologically effective agents such as therapeutic drugs and local anesthetics are suspended in a liquid suspending vehicle which has an elevated viscosity, the viscosity being substantially higher than that of water. Preferred vehicles are non-aqueous liquids and aqueous media which contain a dissolved polymer to increase the viscosity of the vehicle. Regardless of the composition of the media, however, the increased viscosity permits the use of particles of a relatively large size without a loss of suspension stability or localized application. The large particles offer the advantage of a longer release profile, and thus more prolonged activity of the agent.

13 Claims, No Drawings

VISCOUS SUSPENSIONS OF CONTROLLED-RELEASE DRUG PARTICLES

This invention lies in the field of controlled- or sustained-release drug delivery systems. More particularly, this invention relates to particulate suspensions designed for local administration of drugs.

BACKGROUND OF THE INVENTION

Therapeutic drugs, local anesthetics and other agents, which are collectively referred to in this specification as "biologically effective agents" or "drugs", are often topically applied when concentrated, localized action is desired at specifically delineated regions of a patient's anatomy. These regions may be open wounds or any otherwise afflicted areas, such as cavities. The need for this type of administration may for example arise in the treatment of incisional wounds following surgery, or of accidental incisions, punctures, scrapes or bruises, or in the treatment of localized infections such as insect stings or bites, poison ivy, poison oak, or other allergic skin reactions, burns and sunburn, skin rashes and roughness such as dermatitis, psoriasis, and broken or cracked skin in general, as well as more serious traumas such as wounds caused by accidents or recesses or cavities caused by the removal of tumors from bones. The substance to be administered may be a therapeutic agent or a preventive agent, such as, for example, an antibiotic, antibacterial, antifungal, or anti-infective, applied either prior to or subsequent to the onset of the condition, or an analgesic or anesthetic applied either as the sole treatment or in conjunction with additional treatment such as surgery or first aid.

Localized administration has certain advantages over systemic administration. One is the avoidance of adverse side effects, such as those which accompany the use of narcotics and other systemic pain-killers. Another is the faster action and the concentration of the agent's activity at the area where it is needed, i.e., the more economical and efficient use of the agent.

Topical or other localized administrations which are the most effective, however, are those in which the effect of the agent once administered is prolonged over a period of time. In post-surgical applications and accidental wounds, for example, the anesthetic or antibiotic effect supplied by the agent is often needed for a longer period than can be achieved by simple bolus administration of a drug. Many localized skin infections and rashes also require prolonged treatment. One manner in which this has been achieved is by the combination of the biologically effective agent with a polymeric binder to form solid particles of microscopic size. Release of the agent to the environment, i.e., the surface of the wound or afflicted area to which the formulation has been applied, varies with the concentration of the agent in the particle, the size and shape of the particle, and the lattice or pore structure of the polymer binder matrix.

The use of bioerodible polymers adds a further variable affecting the rate of release. Bioerodible polymers are polymers which, upon exposure to bodily fluids or membranes with which they come into contact upon administration, degrade into low molecular weight species which are innocuously absorbed into or excreted by the patient's body. When bioerodible polymers are used, release occurs by any combination of one, two, three or more mechanisms, examples of which mechanisms are the diffusion of the agent through the polymer itself, the diffusion of the agent through the pores in the polymer matrix, and the erosion of the polymer.

The particles are generally of a very small size which permits them to be applied by spraying or injection. For these types of application, the particles are dispersed in a suitable carrier or vehicle such as a low viscosity or volatile liquid. The small particle size has its limitations, however, particularly in the degree to which the particle can prolong the release rate. Due to the high surface area of the particles and the short diffusion path of the agent through each particle, the release of agent from particles small enough to be applied by spraying or injection is often faster than desired.

One solution to this problem is to use particles which consist of the biologically effective agent microencapsulated in a highly diffusion-limiting shell. However, it is difficult to exert the needed control over the manufacture of particle walls of this nature, and if they can be made of bioerodible materials, control of the release rate is rapidly lost once the walls begin to erode.

Larger particles with a longer release profile may be used, provided that they can be applied by means other than a spray nozzle or a syringe with a fine needle. Larger particles may thus be applied as a dispersion in a low-viscosity or volatile liquid carrier by direct spreading of the dispersion over or into the afflicted area, such as the skin or a body cavity, using a brush, sponge, swab or other surface applicator. Particles of this size have a greater tendency to migrate through the carrier once they have been applied, however, thereby coalescing or drawing together, particularly in areas with an uneven surface such as furrows, ridges or bumps. Such migration makes it difficult to achieve an evenly distributed activity of the biologically effective agent over the entire area to which the particles have been applied or to keep them localized to the area to be treated.

One approach to this problem is the use of a thermogel as the carrier, as disclosed by Speaker, T. J., et al., in U.S. Pat. No. 4,917,892, Apr. 17, 1990. The thermogel must be physiologically compatible, and must exist as a fluid at or below room temperature and be convertible to a gel at body temperature. Temperature control is thus important during both preparation and application of the formulation, and at room temperature the dispersion is vulnerable to instability. In addition, premature gel formation will limit the ease of application. Another approach is the incorporation of the particles in a sheet such as a bandage which holds the particles immobile. However, sheets are inappropriate for use in those situations where it is undesirable to leave the sheet behind or where retrieval of the sheet is not possible (e.g., incisional wounds or subcutaneous implants). Sheets are also not very satisfactory for use where the wound to be treated is of a very large or, particularly, irregular shape or has an uneven surface topography, so that it is difficult to cover the wound or difficult to keep it covered with a sheet material. Additionally, sheets, even when erodible, may provide a temporary barrier in the area of a healing wound.

These and other shortcomings and disadvantages of existing systems for controlled-release particulate drug delivery systems are addressed by the present invention.

In EP-A-O 244 188 a controlled release drug delivery system for the periodontal pocket is described. The system comprises microparticles consisting of a drug containing polymer having drug dispersed therein and a fluid suspending medium for the microparticles.

WO-A-92/9226 describes a drug delivery system comprising 1) solid particles comprised of lobeline and a biodegradable polymer and 2) a liquid suspending vehicle.

These and other shortcomings and disadvantages of existing systems for controlled-release particulate drug delivery systems are addressed by the present invention.

SUMMARY OF THE INVENTION

It has now been discovered that particles which provide controlled release of a biologically effective agent can be effectively formulated by dispersion of the particles in a liquid or semi-liquid carrier whose viscosity is substantially greater than that of water. Even though the carrier remains a liquid or semi-liquid prior to, during and subsequent to its application, its high viscosity allows the particles to be evenly distributed over and to be held in place at the area to which the formulation (i.e., the particles and carrier combined) has been applied, regardless of the size of the particles. The fluid state of the carrier further permits the formulation to be readily constituted as a uniform suspension from dry starting materials.

Although not limited as such, the invention is of particular interest with particles which are of a size which makes them unsuitable for application by spraying or hypodermic injection, and instead makes them suitable for application by painting or brushing over the surface to be treated. The invention is also of particular interest as applied to particles utilizing bioerodible polymers as the polymeric matrix which retains the biologically effective agent. The invention is of further interest with the utilization of biodegradable or biocompatible polymers as the viscosity control agent, either alone or dissolved in a carrier liquid.

The invention permits one to control the release rate by varying the size of the particles, and thereby allows one to draw upon a greater size range to achieve the release rate desired for a particular application. As will be seen from the description which follows, in preferred embodiments of the invention, the particle size, composition and other parameters of the system are selected to achieve a release profile which extends the release of fresh agent over a period of at least a day and preferably two or more days.

Further features, advantages and embodiments of the invention will be apparent from the description which follows.

DETAILED DESCRIPTION OF THE INVENTION AND PREFERRED EMBODIMENTS

The liquid carrier whose elevated viscosity maintains the localization and the even distribution of the controlled-release particles in accordance with the present invention may be in any of a wide variety of viscous liquids. Such liquids include aqueous solutions, non-aqueous solutions, and undiluted non-aqueous liquids. Aqueous solutions will be those containing a solute which elevates the viscosity of the solution. Non-aqueous solutions will in general also contain a solute which elevates the solution viscosity, although the solvent is a non-aqueous liquid such as cottonseed oil or any other type of biocompatible oil. Undiluted non-aqueous liquids will be those whose viscosity is in the appropriate elevated range, and this may include non-aqueous solvents such as any type of biocompatible oil or any of a wide variety of bioerodible liquid polymers. Among the many examples are ALZA Corporation's Alzamer® poly(orthoester)s, an example of which is poly(2,2-dioxy-1,6-hexamethylene tetrahydrofuran).

In one preferred embodiment of the invention, carriers are aqueous solutions containing a viscosity-elevating solute. The solute can vary widely. Examples are sugars, oligomers and polymers. Preferred aqueous solutions are those in which the solute is a polymeric species. The polymeric solute of these preferred solutions is any water-soluble polymer which, once dissolved in water, remains dissolved to form a freely-flowing homogeneous liquid solution over the entire temperature range to be encountered by the particle suspension during use, and which imparts sufficient viscosity to the solution to keep solid particles of a wide size range in a substantially uniform suspension. These requirements are met by a wide range of hydrophilic polymers, including polymers of plant or animal origin as well as synthetic polymers. Examples are poly(vinylpyrrolidone); poly(vinyl alcohol); methylcellulose, hydroxypropyl methylcellulose, sodium carboxymethylcellulose, and mixtures of two thereof or all three; sodium alginate; polyacrylamides; polyacrylic acids; collagen; gelatin; polyethylene glycol; polysaccharides and carbohydrates such as starch, cellulose, dextrans and derivatives; thixotropic media; and the like. Among these, hydroxypropyl methylcellulose, sodium carboxymethylcellulose, sodium alginate and poly(vinylpyrrolidone) are presently preferred.

The concentration of the polymeric solute is not critical and may vary widely. Optimal concentrations may vary from one system to the next, depending on the choice of polymer, and the size and quantity of the particles to be suspended. In most applications, polymer concentrations ranging from about 0.1% to about 10% of the aqueous solution on a weight/volume basis (weight in grams per volume in milliliters), preferably from about 0.5% to about 2.0%, will provide the best results. The optimal concentration will generally be selected to achieve a viscosity within a particular range, but this may vary as well.

In another preferred embodiment of the invention, the carriers are chosen from undiluted low molecular weight polymeric materials, such as for example low molecular weight polylactic acid, polyglycolic acid, poly(lactide-co-glycolide) and poly(orthoester)s.

In most applications, optimal viscosities of the system of the invention will range from about 10 to about 2,000,000 centipoise, preferably from about 100 to 500,000 centipoise, and more preferably from about 300 to about 50,000 centipoise, at 37° C. While the benefit of the invention is realized over a broad range of elevated viscosities, the optimal viscosities will be different for different applications. The desired viscosity for any given formulation or use may vary, for example, according to the preference of the physician, the manner of application and type of applicator used, the amount of formulation needed, the area to which the formulation is to be applied, and similar considerations. For incisional wounds or other deep areas, for example, where the formulation is subject to the risk of leakage outward, a higher viscosity vehicle would be preferable for lowering such a risk. For cavities or irregularly shaped areas, such as bone cavities or the exterior surface of arterial walls, where it is desired to have a malleable material that conforms to and retains the shape of the treatment area and be in intimate contact over a large area, an even higher viscosity is preferred. The desired viscosity will also vary with the concentration of the particles in the suspension, since the presence of the particles contributes to the viscosity of the suspension.

As indicated above, the invention is of particular interest for use with particles of a size which is larger than those which are capable of being administered through a spray nozzle or a hypodermic syringe. Thus, the invention is preferred for particles having at least one linear dimension exceeding about 50 microns, more preferred for those having at least one linear dimension exceeding about 100 microns, and even more preferred for those with at least one linear dimension exceeding about 200 microns. The invention also offers benefits to particles of extremely small size, by improving the stability of suspensions of those particles. In certain preferred embodiments, therefore, particles having each linear dimension less than about 1,000 microns are preferred for use with this invention, and the most preferred are those with each linear dimension equal to or less than about 300 microns. The particles may vary considerably in shape. Examples are rods, pellets, cubes, spheres, and discs. Many other possibilities will be readily apparent to those skilled in the art.

The particles will consist of the biologically effective agent in a polymeric binder matrix, together with additional ingredients included on an optional basis. On a molecular scale, the particle may consist of agent and polymer molecules in a randomly distributed arrangement, or the polymer may form a lattice-type structure with the agent occupying the interstices of the lattice. The latter type of structure may be promoted by the use of a pore-forming excipient as one of the optional ingredients referred to above, incorporated in the particles in the process of their formation, the excipient being either extracted from the particles after their formation or retained in the finished particle.

The nature of the biologically effective agent is not critical, and a wide variety of such agents may be used. Biologically effective agents are known in the art. Two prominent classes of such agents which are of particular interest in this invention are therapeutic drugs and local anesthetics. Examples of therapeutic agents are antibacterial, antiviral, antiinflammatory, antifungal, tissue regeneration, tissue growth suppression, and antiprotozoal agents, as well as fluorides, analgesics and disinfecting agents. Examples of local anesthetics are lidocaine, bupivacaine, dibucaine, tetracaine, etidocaine, mepivacaine, ropivacaine, benzocaine, ambucaine, amylocaine, butamben, 2-chloroprocaine, cyclomethycaine, ethyl aminobenzoate, euprocin, levoxadrol, orthocaine, piperocaine and parethoxycaine. Many other examples of both drugs and local anesthetics will be readily apparent to those skilled in the art.

The polymeric binder for retaining the biologically effective agent to form the particles may also vary widely. Both biodegradable and non-biodegradable polymers may be used. Examples of non-biodegradable polymers are polyethylene, polypropylene, polytetrafluoroethylene (Teflon), polycarbonate, polystyrene, polyvinylchloride, poly(ethylene-terephthalate), polysulfones, polyacrylonitrile, polymethylmethacrylate, polyvinylidene chloride, polyvinylidene fluoride, polyamides (such as 6-nylon, 610-nylon, 612-nylon, 12-nylon, and 11-nylon), aromatic polyamides, and polyimides. Biodegradable polymers are presently preferred, and examples are polyhydroxybutyrate, polyhydroxyvalerate, polyhydroxybutyrate-hydroxyvalerate, polyanhydrides, polyorthoesters and polyorthocarbonates. Prime examples of polymers and copolymers of hydroxycarboxylic acids are polymers of d-lactic acid, l-lactic acid, d,l-lactic acid, glycolic acid, and methylethylglycolic acid, copolymers of lactic and glycolic acids, and copolymers of caprolactone and lactic acid. Polyorthoesters and polymers of d,l-lactic acid and copolymers of lactic and glycolic acids are preferred. Polyorthoesters of particular interest are those sold under the trademark Alzamer®, which are disclosed in one or more of the following U.S. patents, all of which are incorporated herein by reference—U.S. Pat. Nos. 4,070,347, 4,093,709, 4,122,158, 4,131,648, 4,138,344 and 4,155,992. A specific example is poly(2,2-dioxy-cis, trans-1,4-cyclohexane dimethylene tetrahydrofuran), a hard solid (glassy) polymer. Further polyorthoesters suitable for use are disclosed in U.S. Pat. No. 4,180,646.

In addition to the polymer and the active agent, the particles of this invention may also include, if desired, one or more diluents, vehicles, stabilizers, buffers, dyes, inert fillers, pigments, and other components of polymeric matrix systems as are known in the art.

In certain cases, a hydrophilic pore-forming excipient is used during the formation of the polymer to form the polymer into a porous structure. When a pore-forming excipient is included, it may be either a solid, a semi-solid or a viscous liquid, and may be organic or inorganic. The pore-forming excipient is combined with the polymeric binder material while the latter is in a liquid form, either prior to cure or subsequent to cure or to formation of the particles. The pore-forming excipient is then retained in the polymer as the particle is being formed and, if necessary, the polymer cured. The excipient may then either be removed from the particle or left in it. If removal is desired, this is achieved by dissolving, extracting, eroding or leaching. Pore-forming excipients capable of use in this method include a wide range of materials. Examples are alkali metal salts such as sodium chloride and potassium chloride; monosaccharides, oligosaccharides and polysaccharides, notably sucrose, glucose, fructose and lactose; polyalcohols such as mannitol and sorbitol; and water-soluble cellulosic polymers such as methyl cellulose and hydroxypropylmethylcellulose.

Other excipients are optionally included. One class of such excipients are inert hydrophobic excipients that act to increase drug delivery and improve reproducibility from certain polymers. Examples of this type of excipient are calcium stearate, magnesium stearate, aluminum stearate, calcium phosphate, myciyl cerotate, β-carotene, zeaxanthin, cholestane, 3-hydroxycholestane, 5,6-cholestene, cholesterol, 3-hydroxy-5,6-cholestene, and 3-amino-5,6-cholestene.

The relative amounts of the components of the particles are not critical and may vary widely. The optimal amount in any particular case will depend on the choice of polymeric binder and its permeability and degradability characteristics, and the choice of biologically effective agent and its desired dosage. In most cases, particles in which the biologically effective agent comprises from about 1% to about 60% by weight of the particle, preferably from about 5% to about 50% by weight, will provide the best results. Likewise, the polymeric binder preferably comprises from about 20% to about 95% by weight, preferably from about 40% to about 85%, of the particle, and the pore-forming excipient may comprise from 0 to about 30% by weight.

The selection of these particle parameters—the relative amounts of the components, the erosion rate of the polymer, whether to include a pore-forming excipient, and the size and shape of the particles—will be done with a view toward achieving a time-release profile which is most suitable for the biologically effective agent used and the reason for application of the composition. Most applications within the contemplation of this invention will extend the release of the agent over a period of one or more days, preferably 2 to 10 days, although different time periods will be preferred for different applications. When the agent is a local anesthetic, for example, and the purpose of the application is to anesthetize post-operational incisional pain, a time period of about three days is optimal. Longer or shorter time periods for other applications will be readily apparent to those skilled in the art.

Formation of the particles may be achieved by any conventional means, which will be readily apparent to those skilled in the art. A particularly convenient method is by forming a viscous liquid mixture of the particle ingredients, and extruding them into solid pellets. The liquid mixture may be formed by dissolving the materials in a suitable solvent to achieve a consistency suitable for extrusion, followed by evaporation of the solvent during the extrusion process. An alternative method is heating the materials to a temperature above their melting points, followed by cooling upon extrusion.

The suspension of the particles in the viscous carrier may be prepared for use in any of a variety of ways. While the suspension may be prepared in advance and stored until needed, such as for example when the carrier is an undiluted non-aqueous liquid, it is often preferable to store the solid and liquid components separately, combining them and reconstituting the suspension only at a time shortly before the suspension is to be used, i.e., one hour or less prior to use, or preferably about fifteen minutes. In such a case, the particles with the biologically effective agent incorporated in their structure will thus be stored separately from the aqueous liquid. The polymeric solute which serves as the viscosity-raising agent of the aqueous liquid may be added as a powder to particles so that when the particles are mixed with water, the polymer dissolves in the water. Alternatively, the polymer can be dissolved in the water prior to the addition of the particles.

Formation or reconstitution of the suspension is achieved by any conventional mixing method, either manually or by the use of mixing equipment. Once the suspension is reconstituted, it may be applied to the application site by any conventional means. This may include manual means alone or with the use of applicators such as swabs, cloths, probes or brushes, or means such as a syringe fitted with a wide-angle or brush-type dispenser, and large-bore hypodermic needles.

In a presently preferred embodiment, the invention finds use in the treatment of wounds. The viscous vehicle allows the active agent-containing particles or minipellets to be easily applied to the wound, using simple application techniques such as for example painting or spreading, or molding or otherwise manupulating manually. The suspension may thus be applied to irregular or large wound areas as easily as to small wounds. Additionally, the viscous vehicle provides an even distribution of the particles over the entire area of the wound and a better retention of the particles over the entire wound for an extended period of time. The wounds which can be treated using the formulation of the invention can range from superficial to deep, from surface to incisional, and from surgical (or otherwise deliberate) to accidental. The formulation is particularly useful for the treatment of incisional wounds, where the particles or minipellets must remain distributed throughout the wound site after the incision has been closed, rather than, for example, flowing out of the wound or settling or aggregating in a portion of the wound such as the bottom of the incision.

The active agent which is initially held in the particles and thereby delivered to the wound can be a local anesthetic, a bactericide or antiseptic, a wound-healing agent, an antiinflammatory, or any other therapeutic or otherwise beneficial agent useful in the healing process.

In a presently preferred embodiment, the active agent is a local anesthetic for treatment of post-operative incisional pain. In current practice, local anesthetics are delivered to post-operative patients by injection, through either a syringe or a catheter. The duration of the anesthetic effect ranges from 2–6 hours, depending upon the specific anesthetic used. When an anesthetic is administered in this manner and its anesthetic effect is needed to last longer than one day, as is the case in many if not most post-surgical procedures, this can only be achieved by administering a solution of the anesthetic repeatedly or continuously to the wound site. This is inconvenient and costly. For post-operational incisional pain, therefore, systemic narcotics are the usual method of treatment, despite their attendant side effects.

By contrast, the particles in the suspensions of the present invention can be formed of a bioerodible polymer which releases a local anesthetic in a controlled manner over an extended period of two or more days, thus substantially increasing the duration of drug action. Because of this long duration of action and the bioerodible nature of the particles, this formulation offers significant advantages over the current treatment method. One such advantage is a reduction or elimination in the use of narcotics and in the adverse side effects associated with narcotics. Another is the ability to achieve the extended effect with a one-time administration. A third is the potentially earlier ambulation of the patient and an earlier release from the hospital. The formulation also offers advantages to the surgeon, including an improved ease of mixing, handling and applying the formulation, and the avoidance of any risk of leaving large foreign bodies in the wound. Furthermore, since the particles are bioerodible, there is no need for a subsequent surgical procedure to retrieve the particles once the anesthetic has been released.

In another presently preferred embodiment, the invention finds use in the treatment of defects in bones, such as those caused by, for instance, traffic accidents or cavities left after tumor removal surgery. While bonewaxes containing drug (but not polymeric drug particles) are known to the art, the liquid-like consistency of such bonewaxes or putties, combined with the unpredictable and irregular shape of the defects to be bridged or filled, virtually prevent the use of the putty or wax itself as a material to control the release rate of the desired agents. Incorporation of solid particles containing the therapeutic agents, according to the present invention, allows one to control the release rate of the agent by virtue of the solid consistency and predetermined shape of the particle, while the wax or putty opens the possibility to spread the particles in the desired configuration over the defect and ensures correct localization of the particles after closure of the wound.

In yet another presently preferred embodiment of the invention, the system of the invention may be utilized in the cardiovascular field to prevent thrombotic and restenotic effects after procedures such as by-pass surgery by placing drug periadventitally (adjacent to but outside the artery) to deliver therapeutically active agents such as heparin. A viscous paste containing solid drug-containing particles can be placed very easily in direct contact with the arterial wall, without any impairment to the artery's mobility, while the solid particles, in which the heparin or other agent is incorporated, will offer excellent, predeterminable control over the release rate of the agent. This is in contrast to presently known periadventitial drug delivery devices, which are gels or solid devices containing a drug (rather than polymeric-drug particles) therein. Whereas the gels are relatively easily placed at the site of the surgery, they do not allow any predetermined control over the release rate of the agent. On the other hand, solid devices offer substantial control overy the release rate, but are very difficult to place into intimate contact with the artery overy a large surface area, preferably covering the entire arterial wall around the vessel. In addition, solid devices will obstruct the natural pulsing motion of arteries when in direct contact with them.

The following examples are offered for purposes of illustration, and are intended neither to limit nor to define the invent in any manner.

EXAMPLE 1

One example of an anesthetic suspension in accordance with this invention is as follows:

particle shape and size: cylindrical, 280µ diameter×500µ length particle constitution: 35% bupivacaine base (by weight), 65% poly(lactic/glycolic acid), referred to in these Examples as "PLGA" (50:50 lactic:glycolic acids, molecular weight 27,000, intrinsic viscosity 0.41 cps)

suspending medium: 0.75% (weight/volume) sodium carboxymethylcellulose, referred to in these Examples as "NaCMC," and 99.25% distilled water; viscosity 400 cps

EXAMPLE 2

This example illustrates the preparation of particles similar to those used in the suspension of Example 1, although a different polymer binder is used.

A mixture of 70% (weight basis) Alzamer® C101ct Bioerodible Polymer (poly(2,2-dioxy-cis,trans-1,4-cyclohexane dimethylene tetrahydrofuran)) and 30% bupivacaine (free base) was prepared in a mixer with a mixing capacity of 8 cc. The components were combined in two steps. As the first step, a fraction of the bupivacaine was mixed into the polymer at 107° C., which is slightly above the melting temperature of the bupivacaine. This fraction amounted to 8% by weight of the mixture, which is close to the saturation point of the melted polymer with bupivacaine. The remaining bupivacaine was then mixed in at 55° C. The resulting mixture was then ground and sieved to a particle size of less than 850µ.

The ground and sieved mixture was then extruded through a ¼-inch extruder, equipped with a 0.3 mm die. The barrel temperature of the extruder was maintained at 54°–72° C., and that of the die at about 65° C. The screw speed was 30 rpm and the current was 2–3.5 amp. A fiber of 0.010–0.015 inch diameter (0.025–0.038 cm) was continuously extruded. The emerging fiber was passed through pinch rollers, and transported continuously to a minipelletizer. Pellets having a diameter of 0.010–0.015 inch (0.025–0.038 cm) and length of 250µ were thus formed.

EXAMPLE 3

This example illustrates the release profile of a local anesthetic from particles prepared by a procedure similar to that of Example 2.

A mixture of 70% (weight basis) PLGA (50:50 lactic:glycolic acids, molecular weight 27,000) and 30% bupivacaine (free base) was prepared in a 25 cc mixer, then ground and sieved through a 20-mesh screen in a manner similar to that described in Example 2. The ground mixture was extruded from a ¼-inch extruder with a ¼-inch die, at a barrel temperature of 150°–190° C. and a die temperature of 195° C. The extrusion produced a fiber of about 11 mils (0.028 cm) in diameter in a continuous strand. The fiber was fed continuously to a pelletizer, and pellets were formed having a diameter of 250–300µ and a length of 450–500µ.

The release of bupivacaine from the pellets was tested by first weighing samples of the pellets, then placing the samples in 20 mL of phosphate-buffered saline (PBS) in scintillation vials. At sampling intervals, aliquots of 2 mL were withdrawn from the vials. Each sampling was followed by the addition of fresh buffer to replace the sample volume. The removed samples were analyzed for their bupivacaine content. Four parallel experiments on the same type of pellet were conducted. In each of the four experiments, bupivacaine was still being released after five days.

EXAMPLE 4

This example illustrates the preparation of anesthetic suspensions in accordance with the present invention, and the handling characteristics of these anesthetics.

The PLGA minipellets of Example 3 containing 30% bupivacaine were suspended in 1.5% NaCMC in distilled water at minipellet loadings of 3, 10 or 30% by the following method.

Each dose of the dry minipellets was placed in a sterile 3 cc syringe. The NaCMC vehicle was drawn to a predetermined value in another sterile 3 cc syringe using a 16–20 gauge needle. The needle was then removed and replaced with a sterile (double) LUER-LOK® connector. The cap and Parafilm® seal were removed from the syringe containing the minipellets (keeping the hub facing upwards), and the two syringes were then connected via the LUER-LOK connector. The plunger in the vehicle syringe was then depressed to force the vehicle into the syringe containing the minipellets, and the resulting suspension was passed back-and-forth through the connector from one syringe barrel to the other a number of times to ensure a homogeneous suspension of pellets in the vehicle. The final exchange placed the suspension in the syringe barrel that originally contained the minipellets, and once this was done the connector was removed. Handling characteristics of the resulting suspensions were then tested by ejecting the suspension from the syringe in 0.5 mL increments and evaluating such factors as flowability, consistency and retention.

In general, as minipellet loading increased, the handling characteristics of the suspension behaved somewhat like a paste rather than a free-flowing liquid. The suspension with 3% minipellet loading behaved similarly to the NaCMC vehicle alone. With 10% loading, little difference was noticed. With 30% loading, the suspension still flowed quite easily, but with a consistency similar to a gel.

EXAMPLE 5

The retention characteristics of the anesthetic suspension of Example 4 were tested as follows.

Linear skin incisions were made in Yucatan micropigs at eight different locations, six on the back and two abdominally. The incisions were 4 cm in length. As each incision was made, 0.5 mL of an anesthetic suspension prepared as described in Example 4 with 3%, 10% or 30% minipellet loading was placed in the wound and the wound was immediately closed. The amount of oozing or displacement of the suspension from each wound was then observed. It was seen that the 30% minipellet suspension, having a substantially higher viscosity than the other two suspensions, was retained in the wound much better than either the 3% or 10% suspension.

EXAMPLE 6

The pharmacological efficacy of a PLGA-bupivacaine anesthetic suspension (15% loading of the PLGA minipellets) as described in Example 1 (except that the suspending medium was 1.5% NaCMC in distilled water) was evaluated using the standard Complete Freund's Adjuvant (CFA) rat model of inflammation.

Three signs of inflammation were assessed. Hyperalgesia was measured by having the plantar surface of the hindpaws of the rats exposed to a beam of radiant heat applied through the glass floor of a testing chamber. Paw withdrawal latency was automatically detected by a photocell. Organized behaviors from which pain and analgesia can be inferred are correlated with withdrawal latency in this model according to a known correlation of Joris, et al. (1987). Edema was determined by measuring the volume of the paw with a plethysmometer (Ugo bastille) 0.001 cc. Hyperthermia was measured by using a 5×7 mm contact thermocouple (YSI, Inc.) applied to the plantar surface of the heel of the hindpaw.

The efficacy of the bupivacaine suspension for blocking hyperalgesia, edema and hyperthermia was evaluated using a repeated-measures dose-response design. CFA (Sigma Chemical Co.) was vortexed in a 1:1.5 emulsion with saline, and a 0.15 mL aliquot was injected sub-cutaneously into the plantar hindpaw of male rats to induce inflammation. Immediately after induction of inflammation, the PLGA minipellets suspension was administered into the injured tissue at doses of 0 (which refers to a NaCMC suspension of polymer particles which did not contain bupivacaine), 0.3, 1.0, 10 and 30 mg in separate groups of rats, with 6–8 rats per group. The effects of the PLGA-bupivacaine suspension were compared to a positive control (indomethacin, at doses of 0, 0.4, 1.3, 4 and 12 mg/kg) administered at the same time to separate groups of rats. Data was collected at baseline and at 4, 8, 12, 24, 36, 48, 60 and 72 hours after induction of inflammation and injection of drugs.

The results show that the PLGA-bupivacaine minipellets in NaCMC vehicle produced a significant and prolonged effect in the rat CFA model, producing a significant dose-related suppression of hyperalgesia. They also produced a suppression of vascular signs of CFA-induced inflammation.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

What is claimed is:

1. A controlled release bupivacaine composition for localized application comprising an even suspension of bupivacaine-containing bioerodible particles in a liquid vehicle, said composition comprising:
    a liquid suspending vehicle having a viscosity ranging from about 10 to about 2,000,000 centipoise at 37° C.; and
    solid, bupivacaine-containing bioerodible polylactic/polyglycolic copolymer particles evenly suspended therein.

2. A composition in accordance with claim 1 in which said liquid suspending vehicle is an aqueous solution of a hydrophilic polymer.

3. A composition in accordance with claim 1 in which said solid particles have one linear dimension which exceeds about 50 microns in length.

4. A composition in accordance with claim 1 in which said solid particles have one linear dimension which exceeds about 100 microns in length.

5. A composition in accordance with claim 1 in which said solid particles have one linear dimension which exceeds about 200 microns in length.

6. A composition in accordance with claim 1 in which said liquid suspending vehicle has a viscosity ranging from about 300 to about 50,000 centipoise at 37° C.

7. A composition in accordance with claim 2 in which the concentration of said hydrophilic polymer in said aqueous solution is from about 0.1% to about 10% on a weight/volume basis.

8. A composition in accordance with claim 2 in which the concentration of said hydrophilic polymer in said aqueous solution is from about 0.5% to about 2% on a weight/volume basis.

9. A composition in accordance with claim 1 in which said solid particles comprise from about 5% to about 30% of said composition.

10. A composition in accordance with claim 2 in which said hydrophilic polymer is a member selected from the group consisting of hydroxpropylmethylcellulose, sodium alginate, sodium carboxymethylcellulose and polyvinylpyrrolidone.

11. A composition in accordance with claim 2 in which said hydrophilic polymer is sodium carboxymethylcellulose at a concentration of from about 0.5%, to about 2.0% in said aqueous solution.

12. A composition in accordance with claim 1 in which said solid particles comprise from about 5% to about 60% by weight of said bupivacaine, the remainder being said bioerodible polylactic/polyglycolic copolymer.

13. A composition in accordance with claim 1 in which said solid particles comprise from about 15% to about 50% by weight of a local anesthetic, the remainder being said bioerodible polylactic/polyglycolic copolymer.

* * * * *